US006303378B1

(12) United States Patent
Bridenbaugh et al.

(10) Patent No.: US 6,303,378 B1
(45) Date of Patent: *Oct. 16, 2001

(54) METHODS FOR PREPARING POLYNUCLEOTIDE TRANSFECTION COMPLEXES

(75) Inventors: Robert Bridenbaugh, Millbrae; Warren Dang, Alameda; Gary Koe, San Mateo, all of CA (US)

(73) Assignee: Valentis, Inc., Burlingame, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 42 days.

(21) Appl. No.: 09/178,371

(22) Filed: Oct. 23, 1998

Related U.S. Application Data

(60) Provisional application No. 60/094,437, filed on Jul. 28, 1998, and provisional application No. 60/063,126, filed on Oct. 24, 1997.

(51) Int. Cl.⁷ .................................................... C12N 15/64
(52) U.S. Cl. ............................................ 435/455; 435/468
(58) Field of Search ..................................... 435/455, 468

(56) References Cited

U.S. PATENT DOCUMENTS

| | | | |
|---|---|---|---|
| 4,450,103 | 5/1984 | Konrad et al. | 530/351 |
| 4,462,940 | 7/1984 | Hanisch et al. | 530/351 |
| 4,623,723 | 11/1986 | Keller et al. | 536/25.4 |
| 4,900,677 | 2/1990 | Hewitt | 435/259 |
| 4,997,932 | 3/1991 | Reardon et al. | 536/25.4 |
| 5,096,818 | 3/1992 | DeBonville | 435/270 |
| 5,209,160 | 5/1993 | Kikyotani et al. | 435/270 |

FOREIGN PATENT DOCUMENTS

| | | |
|---|---|---|
| WO 97/23601 | 7/1997 | (WO) . |
| WO 99/40771 | 8/1999 | (WO) . |

OTHER PUBLICATIONS

Theodossiou et al., "The processing of a plasmid–based gene from *E. Coli*. Primary recovery by filtration", *Bioprocess Engineering*, 16:173–183 (1997).

Marquet et al., "Characterization of Plasmid DNA Vectors for Use in Human Gene Therapy, Part 1", *BioPharm*, 42–50 (1997).

Papamichael et al., "Aqueous Phase Extraction of Proteins: Automated Processing and Recycling of Process Chemicals", *J. Chem. Tech. Biotechnol* 54:47–55 (1992).

Veide et al., "Continuous extraction of β–D–galactosidase from *Escherichia coli* in an aqueous two–phase system: effects of biomass concentration on partitioning and mass transfer", *Enzyme Microb. Technol.*, 6:325–330 (1984).

*Primary Examiner*—John S. Brusca
(74) *Attorney, Agent, or Firm*—Townsend & Townsend & Crew LLP

(57) ABSTRACT

Methods are provided for the preparation of transfection complexes of polynucleotides and polycations, especially cationic lipids, suitable for delivering polynucleotides to cells. In particular, methods are provided for preparing transfection complexes using a reduced-volume, dual-feed process. Complexes are formed upon the collision of two feed stream, containing polynucleotides and polycation, respectively, under conditions resulting in turbulent mixing conditions in minimal volume, and removal of transfection complexes under laminar flow conditions. Alternatively, the components are mixed in a static mixer. The process is easily scaleable and highly reproducible.

8 Claims, 6 Drawing Sheets

METHODS FOR PREPARING POLYNUCLEOTIDE TRANSFECTION COMPLEXES

CROSS REFERENCE TO RELATED APPLICATIONS

This application claims the benefit of U.S. Ser. No. 60/063,126 filed Oct. 24, 1997, and U.S. Ser. No. 60/094,437, filed Jul. 28, 1998, both of which are incorporated herein by reference.

FIELD OF THE INVENTION

This invention relates to preparation of polynucleotide transfection complexes and their use in delivering polynucleotides to cells. In particular, the invention relates to methods for preparing complexes of polynucleotides and polycations suitable for transfecting eukaryotic cells in vivo and in vitro.

BACKGROUND OF THE INVENTION

A number of methods exist for introducing exogenous genetic material to cells, which methods have been used for a wide variety of applications including, for example, research uses to study gene function, and ex vivo or in vivo genetic modification for therapeutic purposes. Ex vivo genetic modification involves the removal of specific cells from an animal, including humans, introduction of the exogenous genetic material, and then re-introduction of the genetically modified cells into the animal. By contrast, in vivo genetic modification involves the introduction of genetic material directly to the animal, including humans, using an appropriate delivery vehicle, where it is taken up by the target cells.

Generally, the various methods used to introduce nucleic acids into cells have as a goal the efficient uptake and expression of foreign genes. In particular, the delivery of exogenous nucleic acids in humans and/or various commercially important animals will ultimately permit the prevention, amelioration and cure of many important diseases and the development of animals with commercially important characteristics. The exogenous genetic material, either DNA or RNA, may provide a functional gene which, when expressed, produces a protein lacking in the cell or produced in insufficient amounts, or may provide an antisense DNA or RNA or ribozyme to interfere with a cellular function in, e.g., a virus-infected cell or a cancer cell, thereby providing an effective therapeutic for a disease state.

Engineered viruses are commonly used to deliver genes to cells. Viral vectors are generally efficient in gene delivery but have certain drawbacks, for example stimulation of an immune response when delivered in vivo. As a result, therefore, a number of non-viral nucleic acid delivery systems have been and continue to be developed. Thus, for example, cationic lipids are commonly used for mediating nucleic acid delivery to cells. See, for example, U.S. Pat. No. 5,264,618, which describes techniques for using lipid carriers, including the preparation of liposomes and pharmaceutical compositions and the use of such compositions in clinical situations. Other non-viral gene delivery systems likewise involve positively-charged carrier molecules, for example, peptides such as poly-L-lysine, polyhistidine, polyarginine, or synthetic polymers such as polyethylimine and polyvinylpyrrolidone.

Nucleic acids are generally large polyanionic molecules which, therefore, bind cationic lipids and other positively-charged carriers through charge interactions. It is believed that the positively charged carriers (or polycations), form tight complexes with the nucleic acid, thereby condensing it and protecting it from nuclease degradation. In addition, polycationic carriers may act to mediate transfection by improving association with negatively-charged cellular membranes by giving the complexes a positive charge, and/or enhancing transport from the cytoplasm to the nucleus where DNA may be transcribed.

For cationic lipid-mediated delivery, the cationic lipids typically are mixed with a non-cationic lipid, usually a neutral lipid, and allowed to form stable liposomes, which liposomes are then mixed with the nucleic acid to be delivered. The liposomes may be large unilamellar vesicles (LUVs), multilamellar vesicles (MLVs) or small unilamellar vesicles (SUVs). The liposomes are mixed with nucleic acid in solution, at concentrations and ratios optimized for the target cells to be transfected, to form cationic lipid-nucleic acid transfection complexes. Alterations in the lipid formulation allow preferential delivery of nucleic acids to particular tissues in vivo. See PCT patent application numbers WO 96/40962 and WO 96/40963.

With respect to any of the polycationic nucleic acid carriers, transfection efficiency is highly dependent on the characteristics of the polycation/nucleic acid complex. The nature of the complex that yields optimal transfection efficiency depends upon the mode of delivery, e.g. ex vivo or in vivo; for in vivo delivery, the route of administration, e.g., intravenous, intramuscular, intraperitoneal, inhalation, etc.; the target cell type, etc. Depending on the use, therefore, different carriers will be preferred. In addition to the choice of polycationic carrier, transfection efficiency will depend on certain physical characteristics of the complexes as well, such as charge and size. These characteristics depend largely on the method by which the complexes are prepared. Particularly for human therapeutic purposes, therefore, it is desirable to have a method of forming the nucleic acid/polycationic carrier complexes in a highly controllable manner. Further, it is desirable to have a process for preparing the complexes which is highly reproducible and scaleable.

The present invention provides these and related advantages as well.

Relevant Literature

Cationic lipid carriers have been shown to mediate intracellular delivery of plasmid DNA (Felgner et al., (1987) Proc. Natl. Acad. Sci. (USA), 84:7413–7416); mRNA (Malone et al., (1989) Proc. Natl. Acad. Sci. (USA) 86:6077–6081); and purified transcription factors (Debs et al., (1990) J. Biol. Chem. 265:10189–10192), in functional form. Literature describing the use of lipids as carriers for DNA include the following: Zhu et al., (1993) Science, 261:209–211; Vigneron et al., (1996) Proc. Natl. Acad. Sci. USA, 93:9682–9686; Hofland et al., (1996) Proc. Natl. Acad. Sci. USA, 93:7305–7309; Alton et al., (1993) Nat. Genet. 5:135–142; von der Leyen et al., (1995) Proc. Natl. Acad. Sci. (USA), 92:1137–1141; See also Stribling et al., (1992) Proc. Natl. Acad. Sci (USA) 89:11277–11281, which reports the use of lipids as carriers for aerosol gene delivery to the lungs of mice. For a review of liposomes in gene therapy, see Lasic and Templeton, (1996) Adv. Drug Deliv. Rev. 20:221–266.

The role of helper lipids in cationic lipid-mediated gene delivery is described in Feigner et al., (1994) J. Biol. Chem. 269(4): 2550–2561 (describing improved transfection using DOPE); and Hui et al., (1996) Biophys. J. 71: 590–599. The effect of cholesterol on liposomes in vivo is described in Semple et al., (1996) Biochem. 35(8): 2521–2525.

The use of cationic peptides and proteins in DNA delivery is described in Emi et al., (1997) Biochem Biophys Res. Comm. 231(2):421–424 (polyarginine); Fritz et al., (1996) Hum. Gene Ther. 7(12):13951404 (histone Hi and SV40 large T antigen nuclear localizing signal); Gao and Huang (1996) Biochemistry 35(3) 1027–1036 (poly-L-lysine, protamine); Legendre and Szoka (1993) Proc. Natl. Acad. Sci USA 90(3):893–897 (gramicidin S); and Niidome et al., (1997) J. Biol. Chem. 272(24):15307–15312 (cationic alpha-helical oligopeptides). Additional transfection facilitating agents are described in Ibanez, et al., (1996) Biochem Cell Biol 74(5):633–643 (spermidine); Budker et al., (1997) Biotechniques 23(1):139 (histone H1 and amphipathic polyamines); and Barthel et al., (1993) DNA Cell Biol. 12(6):553–560 (lipospermine)

A method of preparing cationic lipid/nucleic acid transfection complexes by first forming lipid micelles in the presence of detergent is described in WO 96/37194. Methods of preparing DNA-lipid complexes using polyethylene glycol-phospholipid conjugates and polyamines are described in Hong et al., (1997) 400(2):233–237

SUMMARY OF THE INVENTION

The invention provides a method of preparing a polynucleotide transfection complex, the method comprising providing a feed stream containing a polynucleotide in solution and a second feed stream containing a polycationic carrier in solution, mixing the two feed streams by flowing the mixture through a static mixer. Preferably, the two feed streams converge at a junction and flow through a static mixer located at a minimal distance from the junction and thereby produce polynucleotide transfection complexes.

DESCRIPTION OF SPECIFIC EMBODIMENTS

Figure 1:
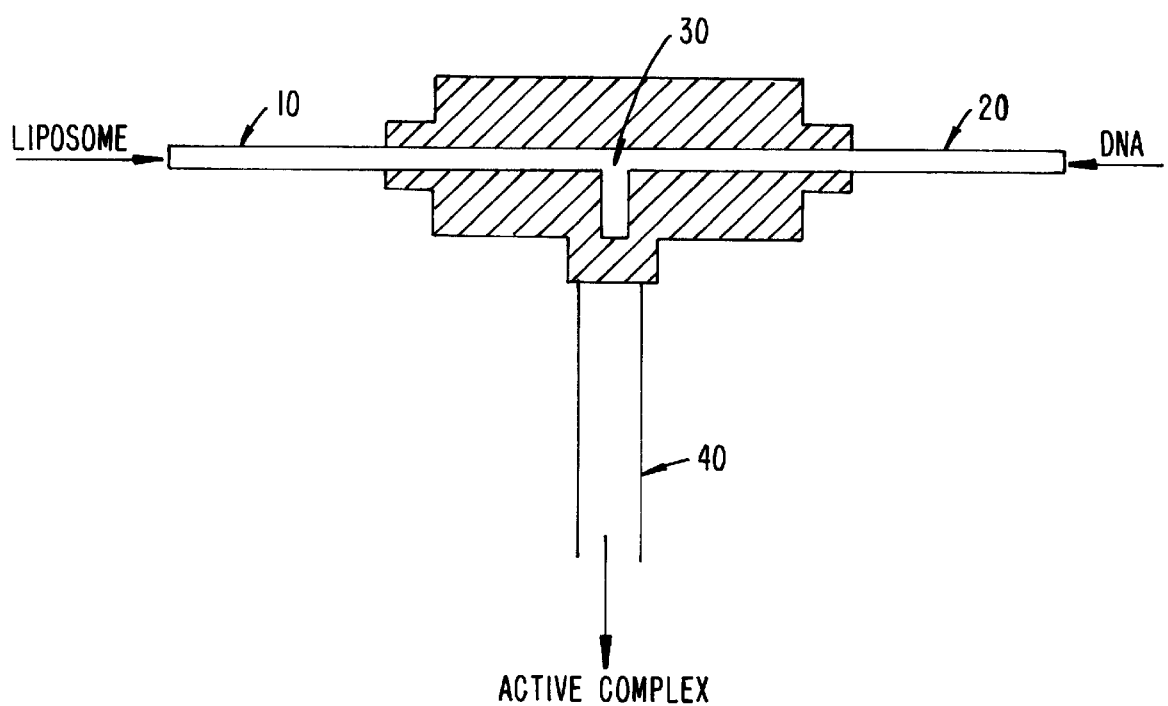
FIG. 1 is a diagram showing the dual feed stream method of polynucleotide transfection complex preparation.
Figure 2:
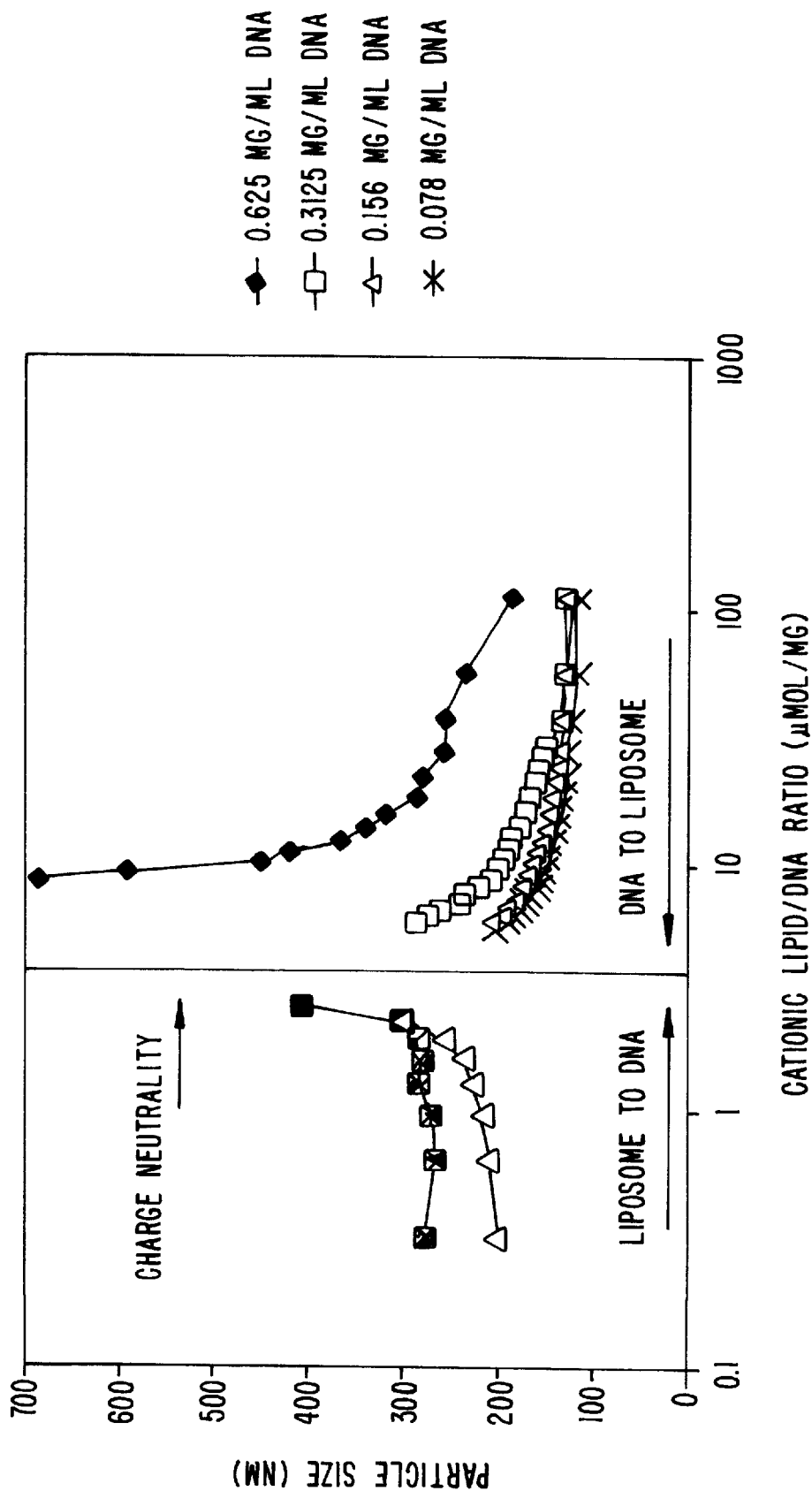
FIG. 2 is a plot of particle size against DNA:cationic lipid ratio. Addition of DNA and liposome to the point of precipitation was performed at increasing concentrations of both components. The target DNA:cationic lipid ratio (1 mg:6(mole) remained constant for each plot. DNA concentrations are presented as the target concentrations for this ratio. The addition of liposome to DNA, and DNA to liposome are shown on the left and right sides of charge neutrality, respectively.

The physical nature of nucleic acid:polycationic carrier transfection complexes is highly dependent on the method in which they are prepared. Typically, transfection complexes are prepared by adding one solution to the other, i.e. nucleic acid to polycation or polycation to nucleic acid, with constant stirring. For in vivo uses, it is desirable to prevent the formation of macroaggregates or precipitation during the complexation process.

The method of preparing polynucleotide transfection complexes described herein is based on a number of observations that have not been previously appreciated. For example, the nature of the transfection complexes is dependent on the concentrations of the nucleic acid and polycation solutions, and larger complexes are formed as the nucleic acid:polycation ratios approach charge neutrality. Also, the kinetics of complex formation are very fast. The complexes so formed are capable of interaction with the starting components. Thus, the nature of interaction between the starting components may be altered by the presence of complexes in the solution. The interference by complexes becomes increasingly significant throughout the complexation process as the concentration of complexes increases within the mixing fluid. In effect, each new addition of starting component (either nucleic acid or polycation) "sees" a different environment of complex/starting component solution.

Accordingly, the method of the present invention allows the nucleic acid and polycationic carrier molecules to react and form complexes in a minimal volume. The complexes thus formed are removed immediately, thereby limiting the interference of complex with the process of complex formation. The process assures adequate mixing of nucleic acid and polycation, while controlling the concentrations of each species in the mixing volume.

In one embodiment, the reduced-volume, dual feed stream process involves the collision of two feed streams (nucleic acid and polycation) in a minimal volume, and the exit of the complex stream away from the site of interaction. The process is highly controllable, reproducible and easily scaleable.

In preferred embodiments, the mixture is flowed through a static mixer to ensure complete mixing of the nucleic acid and polycationic carrier molecule. Static mixers are advantageous because substantially complete mixing can be obtained while minimizing shear of the nucleic acid. In addition, static mixers allow continuous flow, and are readily scalable, allowing for economical preparation of nucleic acid transfection complexes on large scale.

For the purposes of this document, the term "static mixer" refers to any flow-through device which provides enough contact time between two or more liquids to allow substantially complete mixing of the liquids. Typically, static mixers contain an internal helical structure which allows the liquids to come in contact in an opposing rotational flow and causes them to mix in a turbulent or laminar flow. Such mixers are described, for instance, U.S. Pat. No. 3,286,922.

"Transfection" as used herein means the delivery of exogenous nucleic acid molecules to a cell, either in vivo or in vitro, whereby the nucleic acid is taken up by the cell and is functional within the cell. A cell that has taken up the exogenous nucleic acid is referred to as a "host cell", "target cell" or "transfected cell". A nucleic acid is functional within a host cell when it is capable of functioning as intended. Usually, the exogenous nucleic acid will comprise an expression cassette which includes DNA coding for a gene of interest, with appropriate regulatory elements, which will have the intended function if the DNA is transcribed and translated, thereby causing the host cell to produce the peptide or protein encoded therein. DNA may encode a protein lacking in the transfected cell, or produced in insufficient quantity or less active form, or secreted, where it may have an effect on cells other than the transfected cell. Other examples of exogenous nucleic acid to be delivered include, e.g., antisense oligonucleotides, mRNA, ribozymes, or DNA encoding antisense RNAs or DNA/RNA chimeras. Nucleic acids of interest also include DNA coding for a cellular factor which, when expressed, activates the expression of an endogenous gene.

"Transfection efficiency" refers to the relative number of cells of the total within a cell population that are transfected and/or to the level of expression obtained in the transfected cells. It will be understood by those of skill in the art that, by use of appropriate regulatory control elements such as promoters, enhancers and the like, the level of gene expression in a host cell can be modulated. The transfection efficiency necessary or desirable for a given purpose will depend on the purpose, for example the disease indication for which treatment is intended, and on the level of gene expression obtained in the transfected cells.

"Polycation" refers to any molecular entity having multiple positive charges, which, when combined with nucleic acid, interacts by ionic interactions with the nucleic acid. "Polycationic carrier" refers to a polycation which, when combined with a polynucleotide, forms a complex suitable for transfecting eukaryotic cells. For example, cationic lipids have been shown to be efficient polycationic carriers for nucleic acid delivery to cells. Typically, cationic lipid carriers are in the form of liposomes having both cationic and non-cationic lipid (usually neutral lipid) components. Thus, a "lipid carrier" or "cationic lipid carrier" refers to a lipid composition of one or more cationic lipids and, optionally, one or more non-cationic lipids for delivering agents to cells. The lipid carrier may be in any physical form including, e.g., liposomes, micelles, interleaved bilayers, etc.

The term "cationic lipid" is intended to encompass lipids that are positively charged at physiological pH, and more particularly, constituitively positively charged lipids comprising, for example, a quaternary ammonium salt moiety. Cationic lipids used for gene delivery typically consist of a hydrophilic polar head group and lipophilic aliphatic chains. Similarly, cholesterol derivatives having a cationic polar head group may also be useful. Farhood et al., (1992) Biochim. Biophys. Acta 1111:239–246; Vigneron et al., (1996) Proc. Natl. Acad. Sci. (USA) 93:9682–9686.

Lipid carriers usually contain a cationic lipid and a neutral lipid, usually in approximately equimolar amounts. The neutral lipid is helpful in maintaining a stable lipid bilayer in liposomes, and can significantly affect transfection efficiency. The liposomes may have a single lipid bilayer (unilamellar) or more than one bilayer (multilamellar). They are generally categorized according to size, where those having diameters up to about 50 to 80 nm are termed "small" and those greater than about 80 to 1000 nm, or larger, are termed "large." Thus liposomes are typically referred to as large unilamellar vesicles (LUVs), multilamellar vesicles (MLVs) or small unilamellar vesicles (SUVs). Methods of producing cationic liposomes are known in the art. See, e.g., Liposome Technology (CFC Press, NY 1984); Liposomes by Ortro (Marcel Schher, 1987); Methods Biochem Anal. 33:337462 (1988).

Cationic lipids of interest include, for example, imidazolinium derivatives (WO 95/14380), guanidine derivatives (WO 95/14381), phosphatidyl choline derivatives (WO 95/35301), and piperazine derivatives (WO 95/14651). Examples of cationic lipids that may be used in the present invention include DOTIM (also called BODAI) (Solodin et al., (1995) Biochem. 34: 13537–13544), DDAB (Rose et al., (1991) BioTechniques 10(4):520–525), DOTMA (U.S. Patent No. 5,550,289), DOTAP (Eibl and Wooley (1979) Biophys. Chem. 10:261–271), DMRIE (Felgner et al., (1994) J. Biol. Chem. 269(4): 2550–2561), EDMPC (commercially available from Avanti Polar Lipids, Alabaster, Alabama), DCChol (Gau and Huang (1991) Biochem. Biophys. Res. Comm. 179:280–285), DOGS (Behr et al., (1989) Proc. Natl. Acad. Sci. USA, 86:6982–6986), MBOP (also called MeBOP) (WO 95/14651), and those described in WO 97/00241. Particularly preferred are EDMPC for aerosolized delivery to airway epithelial cells, and DOTIM, DOTAP or MBOP for intravenous delivery to vascular endothelial cells of various organs, particularly the lung. In addition, cationic lipid carriers having more than one cationic lipid species may be used to produce complexes according to the method of the present invention.

Neutral lipids of use in transfection complexes are known, and include, for example, dioleoyl phosphatidylethanolamine (DOPE), Hui et al., (1996) Biophys. J. (71):590–599; cholesterol, Liu et al., (1997) Nat. Biotech. (15):167–173; and dilauroyl phosphatidylethanolamine (DLPE) (co-pending patent application serial no. 08/832,749). Normally, cationic lipid and non-cationic lipids are used in approximately equimolar amounts.

Additional polycationic carriers include positively charged peptides and proteins, both naturally occurring and synthetic, as well as polyamines, carbohydrates or synthetic polycationic polymers. Examples include polylysine, polyarginine, protamnine, polybrene, histone, cationic dendrimer, and synthetic polypeptides based on viral peptides, e.g., having cell binding, endosomal release or nuclear localizing functions, etc. For certain applications, polycationic carriers may include cationic lipid as well as peptide moieties. See, e.g., WO 96/22765.

The nucleic acid may be in any physical form, e.g., linear, circular or supercoiled; single-stranded, double-, triple-, or quadruple-stranded; and further including those having naturally occurring nitrogenous bases and phosphodiester linkages as well as non-naturally occurring bases and linkages, e.g. for stabilization purposes. Preferably it is in the form of supercoiled plasmid DNA. Plasmid DNA is conveniently used for DNA transfections since there are no size constraints on the DNA sequences that may be included, and it can be produced in large quantity by growing and purifying it from bacterial cells.

"Transfection complex" or "polynucleotide transfection complex" refers to a combination of a polycationic carrier and a nucleic acid, in any physical form, for use in transfecting eukaryotic cells. A transfection complex may include additional moieties, e.g., targeting molecules such as receptor ligands or antibody fragments, or other accessory molecules. For example, nuclear localizing peptides may be included for facilitating transport of the polynucleotide to the cell nucleus. Kalderon et al., (1984) Cell 39:499–509;

Chelsky et al., (1989) Mol. Cell Biol. 9:2487–2492; Dingwall & Laskey (1991) Trends Biochem. Sci. 16:478–481. Proteins or peptides may be included in the transfection complex to facilitate release of the transfection complex from the endosome after internalization. Raja-Walia et al., (1995) Hum. Gene Therap. 2:521–530; Bai et al., (1993) J. Virol. 67:5198–5205. In addition, enzymes involved in transcription and/or translation may be included to facilitate gene expression in the cell cytoplasm without transport to the cell nucleus. Gao & Huang (1993) Nucl Acids Res. 21:2867–2872.

The transfection complexes may also be prepared to include a targeting moiety, to target delivery of the complex to the desired target cell in vivo. Thus, strategies are known in the art for including receptor ligands for delivery to cells expressing the appropriate receptor, or using antibodies or antibody fragments to target transfection complexes to cells expressing a specific cell surface molecule. See WO 96/37194; Ferkol et al., (1993) J. Clin. Invest. 92:2394–2400.

The polycationic carriers and polynucleotide molecules are mixed, resulting in polynucleotide transfection complexes. In addition to the mixing conditions, the physical structure of such complexes depends on the polycationic carrier and nucleic acid components, the ratios between them, concentrations of each, buffer ionic strength, and the like. The polycationic carriers are mixed with nucleic acids in aqueous solution, at concentrations and ratios optimized for the target cells to be transfected.

For preparation of cationic lipid/polynucleotide complexes, the cationic lipids will typically be in the form of liposomes. The lipid mixtures typically are prepared in chloroform, dried, and rehydrated in, e.g., 5% dextrose in water or a physiologic buffer to form liposomes. Low ionic strength solutions are preferred. Liposomes may be LUVs, MLVs, or SUVs. Usually, the liposomes formed upon rehydration are predominantly MLVs, and SUVs are formed from them by sonication or by extrusion through membranes with pore sizes ranging from 50 to 600 nm to reduce their size. Most preferably, the liposomes are extruded through a series of membranes with decreasing pore sizes, e.g., 400 nm, 200 nm and 50 nm.

The nucleic acid will usually be plasmid DNA, prepared in a low ionic strength solution to prevent interference by additional ions with the complexation process. A low-ionic strength solution means a solution having a conductivity less than about 35 mS, preferably less than about 10 mS, and most preferably less than about 1 mS. Desirably, the DNA solution will contain no salts. Preferably the DNA is in a solution of about 5% dextrose in 5 mM Tris-HCl (pH 8.0).

The nucleic acid and polycationic carrier solutions are prepared separately at the desired concentrations, and provided in two feed streams. In one embodiment, illustrated in FIG. 1, the two feed streams 10, 20 collide at a Tee junction 30. The complexes formed upon the mixing of the two solutions within the Tee junction 30, exit away from the site of interaction.

The tubing size and flow rate are chosen to provide adequate mixing at the Tee. Turbulent flow is determined by the Reynold's number, Re, calculated according to the equation:

$$Re = Dv\rho/\mu$$

where D is the diameter of the tubing (cm), v is the flow velocity (cm/sec), $\rho$ is the density of the solution (g/ml), and $\mu$ is the viscosity of the solution (centipoise). The transition regime from laminar to turbulent flow exists at 2,100 <Re< 3,000. Bird, Stewart, and Lightfoot, Transport Phenomena (John Wiley & Sons, Inc., NY, 1960), p. 108.

The parameters chosen should provide for mixing under turbulent conditions. Thus, the input feed streams may be provided under turbulent flow conditions, or they may be provided under laminar flow conditions, provided that turbulent mixing results from the colliding of the streams. In some embodiments flow rate is selected to provide laminar flow in the input streams, but turbulent flow conditions at the Tee junction. Generally, tubing sizes and inlet flow rates for both nucleic acid and polycationic carrier solutions, are selected such that the outlet velocity is at least about 7.5 cm/sec, , usually at least about 10 cm/sec, and often at least about 20 cm/sec. When expressed in terms of Reynolds values, the outlet solution preferably has Re at least about 180 and usually at least about 250, and often greater than about 500. When the solutions are provided under turbulent flow conditions, the Re value for the nucleic acid solution will have an upper limit at the point where the nucleic acid exhibits degradation due to shearing. Re values up to at least about 7100 do not cause degradation of the nucleic acid.

One of skill will recognize that the flow rates or Reynolds values of the polycationic carrier solutions need not be the same as those of the nucleic acid solutions. Examples of flow rates suitable for use in the present invention are provided in Example 4, below. The parameters listed below produce Re which lie within the laminar flow range, Re=1870, and turbulent mixing results from the colliding streams. The tube diameter and velocity correspond to a flow rate of approximately 70 ml/min.

D=1/32"=0.079 cm v=235.77 cm/sec $\rho \cong 1.00$ g/cc $\mu \cong 1.00$ centipoise The product stream, 40, is designed such that laminar flow develops as a consequence of a larger tube diameter. In the above example, a tube diameter of 3/32"=0.238 cm results in laminar flow conditions. Laminar flow reduces intra-stream mixing and the interaction between the formed polycation/nucleic acid complexes. The product stream will settle into fully-developed laminar flow and the turbulent effects of mixing will diminish when the tube length exceeds Le, equivalent length of discharge pipe. Perry and Green, Perry's Chemical Engineering Handbook, Sixth Edition (McGraw-Hill Inc., NY 1984), pp. 5–34. The correlation between Re, D, and Le is given by the following equation:

$$Le = 0.035D \, Re$$

In the above example, the product stream tube, 40, length is 25.4 cm, which exceeds the required Le of approximately 10.4 cm. Product is collected after laminar flow has developed. This ensures that product interaction is minimized immediately after it is formed.

The feed streams may be provided in other orientations, besides the Tee junction in the above example, as long as the polynucleotide and polycation are thoroughly mixed. For example, the feed streams may be provided in a Y-junction, or as concentric cylinders, or feed into a static mixer. In addition, more than two feed streams may be provided, if desired, for example, where the final transfection complexes will contain three or more components.

As noted above, static mixers can also be used to prepare the complexes. In these embodiments, the static mixer is connected at a minimal distance downstream of a junction of the nucleic acid solution and the polycationic carrier solution. Adequate mixing, important in preventing the formation of large particulates (>1 (m), becomes limiting when the volume of the mixing container is increased. A static mixer is employed to allow sufficient mixing of the nucleic acid and polycationic carrier components, while reducing shear stress and thus nucleic acid degradation associated with rigorous mixing conditions. Static mixers are particularly preferred when large volumes, e.g. volumes greater than one liter, are mixed.

The degree of mixing is controlled by varying the flow rate of the solutions through the mixer, the type of mixer used, the diameter of the mixer, and the number of elements in the mixer. A laminar flow static mixer is preferred. For instance, in the preparation of transfection complexes of the invention a Kenics laminar flow static mixer (7 inches long, 21 element, 0.250 inch outer diameter, 0.187 inch inner diameter, 316L stainless steel) is connected down stream of a junction where the two feed streams converge. Feed stream #1, comprised of a polynucleotide solution and feed stream #2, comprised of a polycationic carrier solution, or dispersion, flow into the junction at typical linear velocities of 0.17 to 0.77 feet per second, corresponding to flow rates between about 50 and 250 ml/min, and preferably between about 100 and 180 ml/min. The static mixer should contain at least 21 elements, and may have up to 36 elements.

The combined streams are immediately fed into the static mixer to enhance mixing between the two streams and formation of the transfection complexes. The resulting mixture containing the polynucleotide transfection complexes is collected from the static mixer exit stream. Alternatively a turbulent flow static mixer may be used (e.g., a Komax static mixer with 21 elements, 5 inches long, ¼ inch outer diameter, 0.194 inch inner diameter, 316L Stainless steel). The linear velocity, however, must be reduced significantly to avoid shearing the nucleic acid when using a turbulent flow static mixer. Alternative static mixers may be obtained from Statomix (Conprotec, Inc., Salem, N.H.), ranging in length from 6 to 10 ½ inches, outer diameters from 0.188 to 0.25 inches, and inner diameters from 0.132 to 0.194 inches, and 24 to 36 elements. By using the analytical methods described herein, the nucleic acid integrity can be monitored through a rarige of linear velocities to determine the conditions allowing acceptable throughput and acceptable product quality.

Figure 7:
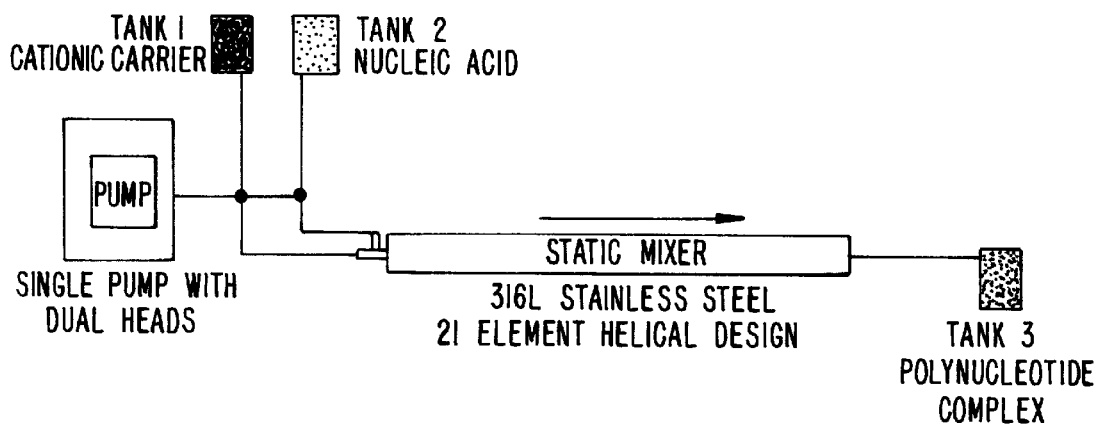
FIG. 7 is a diagram showing the methods of the invention using a static mixer.

FIG. 7 shows an exemplary system in which a static mixer is used to provide complete mixing of the nucleic acid and the polycation.

Tank 1 contains the polycationic carrier solution or dispersion and Tank 2 contains the nucleic acid solution. The pump is started and flow moves simultaneously through both lines and through the Tee junction. The two resultant streams are radially mixed by the static mixer helical elements and polynucleotide complexes are formed and collected in a sterile container. Initial concentrations and flow rates from Tank 1 and Tank 2 can be adjusted to achieve the desired ratio of polycationic carrier to nucleic acid in the resulting transfection complexes.

A number of analytical methods are known for characterizing the complexes prepared according to the method of the invention. Visual inspection may provide initial information as to aggregation of the complexes. Spectrophotometric analysis may be used to measure the optical density, giving information as to the aggregated status of the complexes; surface charge may be determined by measuring zeta potential; agarose gel electrophoresis may be utilized to examine the amounts and physical condition of the polynucleotide molecules in the complexes; particle sizing may be performed using commercially available instruments; HPLC analysis will give additional information as to resulting component ratios; and dextrose or sucrose gradients may be used to analyze the composition and heterogeneity of complexes formed.

It will be appreciated that using the method of complex preparation described herein, polynucleotide transfection complexes may be prepared in a variety of formulations depending of the desired use. Uses contemplated for the complexes of the invention include both in vivo and in vitro transfection procedures corresponding to those presently known that use cationic lipid and other cationic carriers, including those using commercial cationic lipid preparations, such as Lipofectin, and various other published techniques using conventional cationic lipid technology and methods. See, generally, Lasic and Templeton (1996) Adv. Drug Deliv. Rev. 20: 221–266 and references cited therein. Thus, the ratios of each component in the complexes, final concentrations, buffer solutions, and the like are easily adjusted by adjusting the starting components. The method allows the resulting transfection complexes to the prepared in a highly controlled fashion, efficiently using starting materials and yielding active transfection complexes.

Cationic lipid-nucleic acid transfection complexes can be prepared in various formulations depending on the target cells to be transfected. See, e.g., WO 96/40962 and WO 96/40963. While a range of lipid-nucleic acid complex formulations will be effective in cell transfection, optimum conditions are determined empirically in the desired experimental system. Lipid carrier compositions may be evaluated by their ability to deliver a reporter gene (e.g. CAT which encodes chloramphenicol acetyltransferase, luciferase, alkaline phosphatase or β-galactosidase) in vitro, or in vivo to a given tissue in an animal, such as a mouse.

For in vitro transfections, the various combinations are tested for their ability to transfect target cells using standard molecular biology techniques to determine DNA uptake, transcription and/or protein production, including Southern blot analysis, Northern blot analysis, Western blot analysis, PCR, RT-PCR, ELISA and reporter gene activity assays. Typically, in vitro cell transfection involves mixing nucleic acid and lipid, in cell culture media, and allowing the lipid-nucleic acid transfection complexes to form for about 10 to 15 minutes at room temperature. The transfection complexes are added to the cells and incubated at 37(C. for about four hours. The complex-containing media is removed and replaced with fresh media, and the cells incubated for an additional 24 to 48 hours.

In vivo, particular cells can be preferentially transfected by the use of particular cationic lipids for preparation of the lipid carriers, for example, by the use of EDMPC to transfect airway epithelial cells (WO 96/40963) or by altering the cationic lipid-nucleic acid formulation to preferentially transfect the desired cell types (WO 96/40962). Thus, for example, in circumstances where a negatively charged complex is desired, relatively less cationic lipid will be complexed to the nucleic acid resulting in a higher nucleic acid to cationic lipid ratio. Conversely, in circumstances where a positively charged complex is desired, relatively more cationic lipid will be complexed with the nucleic acid, resulting in a lower nucleic acid to cationic lipid ratio.

The lipid mixtures are complexed with DNA in different ratios depending on the target cell type, generally ranging from about 6:1 to 1:20 (g DNA:nmole cationic lipid. For transfection of airway epithelial cells, e.g., via aerosol, intratracheal or intranasal administration, net negatively charged complexes are preferred. Thus, preferred DNA:cationic lipid ratios are from about 10:1 to about 1:20, preferably about 3:1. For intravenous administration, preferred DNA:cationic lipid ratios range from about 1:3.5 to about 1:20 (g DNA: nmole cationic lipid, most preferably, about 1:6 to about 1:15 (g DNA: nmole cationic lipid. Additional parameters such as nucleic acid concentration, buffer type and concentration, etc., will have an effect on transfection efficiency, and can be optimized by routine experimentation by a person of ordinary skill in the art Delivery can be by any means known to persons of skill in the art, e.g., intravenous, intraperitoneal, intratracheal, intranasal, intramuscular, intradermal, etc. PCT patent application WO 96/40962 describes the preparation and use of cationic lipid carriers for in vivo DNA delivery. For aerosol administration, via intranasal or intraoral delivery, the cationic lipid-nucleic acid transfection complex will withstand both the forces of nebulization and the environment within the lung airways and be capable of transfecting lung cells. Techniques for delivering genes via aerosol administration of cationic lipid-DNA transfection complexes is described in U.S. Pat. No. 5,641,662.

The following examples are offered by way of illustration and not by way of limitation.

EXAMPLES

Example 1

Preparation of DNA and Liposomes

Plasmid p4119 containing the CAT reporter gene under the control of the HCMV promoter was prepared at a concentration of 5 mg/ml in 10 mM Tris-HCl. Cholesterol (Sigma, St. Louis, Mo.) and DOTIM (Sigma) were dissolved in chloroform (EM Sciences, Gibbstown, N.J.) at a 1:1 mole ratio, and lipid films were formed with a rotary evaporator. The films were hydrated with 5% (w/v) dextrose in water (D5W) at room temperature and extruded through a series of membranes having pore sizes of 400 nm, 200 nm, and 50 nm. Liposomes were prepared in a concentration of 40 mM in D5W. The final concentration of DOTIM and cholesterol in the liposome dispersion was determined by HPLC to be 16.4 mM DOTIM and 16.9 mM cholesterol.

Approximately 25 mg of DNA was dialyzed overnight into 2 L of 2.5 mM histidine (Sigma) in D5W (pH 6.0). The concentration of DNA was determined by absorbance at 237 nm and adjusted to 0.625 mg/ml.

Example 2

Titration of DNA and Liposomes to the Point of Precipitation 1 ml of liposome solution (3.75 mM DOTIM) was aliquoted into a 4 ml vial and stirred gently. A 50 $\mu$l aliquot of DNA solution was added and allowed to stir for approximately 5 min. A 10 $\mu$l sample was removed and diluted 30X in D5W for particle sizing information. DNA addition and sampling were repeated until aggregates were visible to the naked eye. Particle size data was obtained using a NiComp 370 sub-micron particle sizer (Particle Sizing Systems Inc., Santa Barbara, Calif.). The titration procedure was repeated using initial DOTIM concentrations of 1.875 mM and 7.5 mM. The concentration of the DNA was varied to maintain a constant DNA:lipid ratio. Titration of liposome to DNA was performed in the same manner.

FIG. 2 shows the average vesicle size produced by titration of starting components. We observe that the onset of precipitation begins at vesicle sizes of approximately 240 nm. As the DNA/liposome ratios approach 1:3 mg DNA:glmol cationic lipid (theoretical charge neutrality), the complexes begin to precipitate. We hypothesize that the reduced ionic interaction allows shorter range van der Waals forces to domninate, causing complex particles to aggregate. In order to prevent the formation of large aggregates and eventually precipitation, DNA/liposome complexes must either carry net ionic charges to repel one another, or steric constraints beyond which van der Waals forces are no longer effective (e.g., Stealth liposomes, Lasic, 1997).

Titration experiments show that the DNA/liposome complexes begin to precipitate much earlier than the theoretical 1:3 ratio. Even with formulations designed to carry a net positive charge to prevent precipitation, the driving force toward charge neutrality can cause the formation of near neutral complexes in local environments. DNA's affinity for complexes competes with its affinity for free liposomes. This interference by the end product becomes increasingly significant as more product is formed. The complexes formed using this method leads to inefficient use of liposome, and may result in aggregate-prone complexes. A condition that promotes the formation of more uniform complexes minimizes the interference of product on the interaction between starting components.

Example 3

Comparison of Different DNA/Liposome Complexation Methods

Method 1. DNA at a concentration of 0.625 mg/ml was added to a mixing solution of DOTIM/cholesterol liposomes (DOTIM concentration 3.75 mM), stirred in a glass vial at 500 rpm. An equal volume of DNA was dispensed at a rate of 37.5 ml/min, and allowed to mix for 20 seconds. The final DNA and DOTIM concentrations were 0.3125 mg/ml and 1.875 mM respectively. Final DNA:cationic lipid ratio was 1:6 (pg DNA:nmole cationic lipid). Complexes were also prepared by the same method at a final DNA:cationic lipid ratio of 1:12 ($\mu$g DNA:nmole cationic lipid).

Method 2. Complexes were prepared as described for Method 1, except that the DNA was added to the liposome solution at the rate of 6 ml/min.

Method 3. A 10 ml solution of DNA (0.625 mg/ml) was loaded into a 60 ml Becton-Dickinson plastic syringe. A 10 ml liposome solution (DOTIM concentration 3.75 mM) was prepared and loaded into a separate syringe. The two syringes were connected through PTFE tubing (ID=1/32"; OD=1/16") to opposite ends of a PTFE Tee. The Tee outlet was connected to a 25.4 cm long section of PTFE tubing (ID=3/32"; OD=5/32"). The syringes were loaded into a programmable multi-syringe pump (Cole Parmer Instrument Co., Vernon Hills, Ill.). The contents of the syringes were simultaneously pumpled at a rate of 70 ml/min through the Tee and collected from the outlet tube into a sterile container. The holdup contents were discarded. The final DNA and DOTIM concentrations were 0.3125 mg/ml and 1.875 mM respectively (1:6 ratio ($\mu$g DNA:nmole cationic lipid)). Using this method, DNA/liposome complexes were also prepared at final concentrations of 0.3125 mg/ml DNA and 3.75 mM DOTIM (1:12 ratio ($\mu$g DNA:nmole cationic lipid)).

Methods for characterization of DNA/liposome complexes include spectrophotometric analysis at 400 nm, zeta potential analysis using a Brookhaven Zetaplus (Brookhaven Instruments, Holtsville, N.Y.), particle sizing using a NiComp 370, and dextrose density centrifugation (described below). In addition, in vivo transfection activity of the complexes was determined by CAT expression in the lungs of ICR mice 24 hr after a 200 μl IV tail vein injection. CAT expression was determined by ELISA assay and normalized to the amount of total protein (ng CAT/mg total protein).

Dextrose gradients (5% w/v to 20% w/v) were prepared using the BioComp Gradient Master (BioComp Instruments, Inc., New Brunswick, Canada). At room temperature, centrifuge tubes (12 ml) were half-filled with 5% dextrose followed by careful addition of 6 ml of 20% dextrose to the bottom of the tube with a syringe and canula. The tubes were placed in the Gradient Master and programmed to produce the linear gradients (time=2 min 25 sec., angle=81.5°, speed setting=15). The gradients were allowed to equilibrate to 5° C. for 1–2 hrs. Approximately 200 μl sample was loaded to the top of the gradient, and spun for 1 hr at 40,000 rpm and 4° C. using a Beckman −70 ultracentrifuge with a SW-41 rotor. The centrifuged gradients were loaded into a tube piercing apparatus (Brandell) and 30 % w/v dextrose was pumped at 1 ml/min into the bottom of the tube. The contents of the tube were forced through an on-line U/VIS spectrophotometer (Rainin) and absorbance was measured at 237 nm (DOTIM absorbance).

Table 1 compares the optical density ($OD_{400}$), particle size and zeta potential of the complexes prepared using the three methods. Method 2 complexes have higher $OD_{400}$ values, larger average particle sizes, and lower zeta-potential values compared with methods 1 and 3. This suggests that complexes produced using method 2 are more aggregated and have a lower net positive charge, consistent with formation of near neutral complexes. There is no apparent difference in the characteristics of complexes prepared using methods 1 and 3.

TABLE 1

Characterization: optical density ($OD_{400}$), particle size, and zeta potential of complexes. Optical density is expressed as the absorbance at 400 nm wavelength for a sample diluted 1:20 in 5% w/v dextrose. Particle size is represented by the mean diameter of a complex solution diluted 1:30 in 5% w/v dextrose. Zeta-potential is obtained from a 1:10 dilution of a complex solution in purified water.

| Method | DNA:cationic lipid ratio (mg/μmol) | $OD_{400}$ (absorbance) | Particle size (nm) | Zeta-potential (mV) |
|---|---|---|---|---|
| 1 | 1:6 | 0.183 | 238 | 45.8 |
| 2 | 1:6 | 0204 | 338 | 39.7 |
| 3 | 1:6 | 0.172 | 227 | 45.4 |
| 1 | 1:12 | 0.171 | 207 | 45.9 |
| 2 | 1:12 | 0.206 | 274 | 39.0 |
| 3 | 1:12 | 0.160 | 206 | 39.6 |

Figure 3:
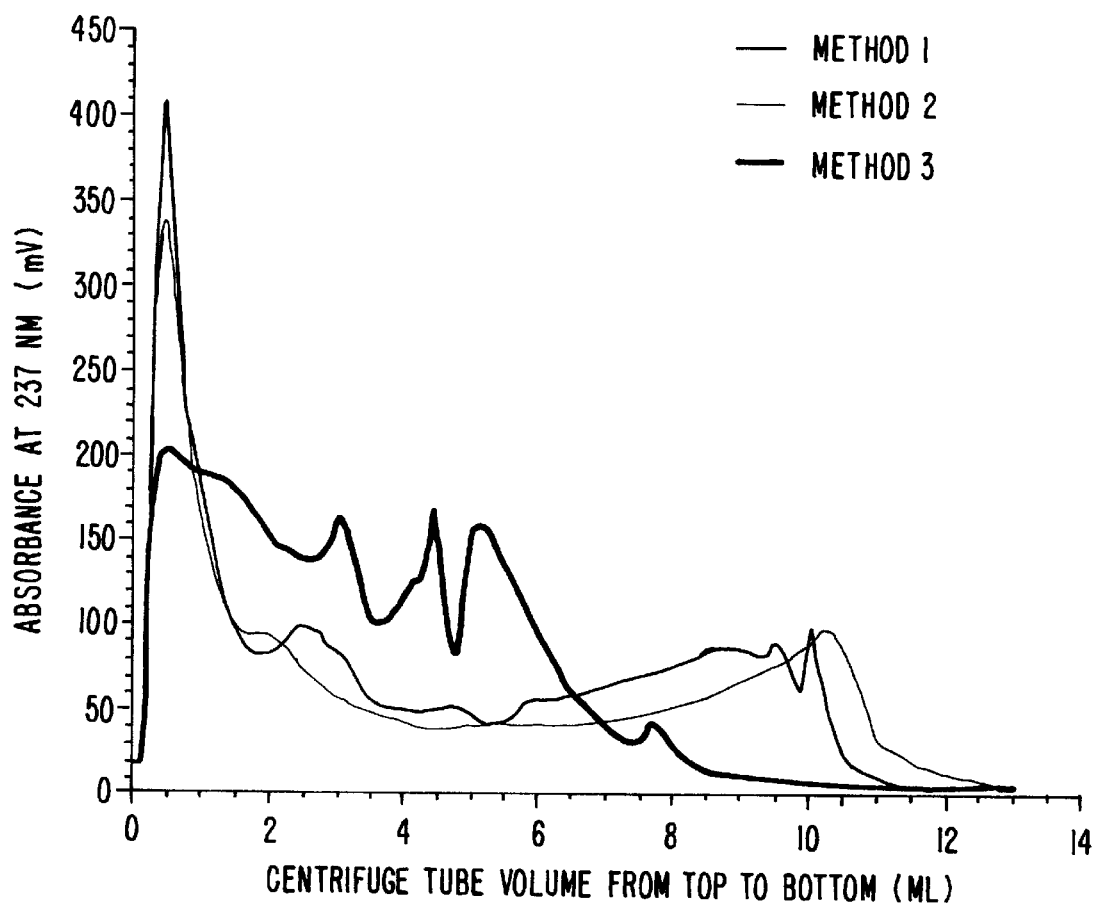
FIG. 3 shows the density gradient profiles of DNA:cationic lipid complexes (1:6 ratio). Profiles are measured by flow-cell UW spectrophotometer at 237 nm. The contents of the centrifuged samples (approx. 13 ml) are pumped through the flow-cell at a rate of 1 ml/min. The ordinate represents the approximate location within the centrifuge tube.

FIG. 3 shows the profiles of DNA/liposome complexes (1:6 DNA/lipid ratio) prepared by the three methods. These profiles show significant differences in the types of DNA/liposome populations. Free liposomes settle at the top of the gradient, and generally do not penetrate further into it. The data show that, for methods 1 and 2, a large peak associated with free liposomes resides at the top of the gradient, while method 3 produces significantly less free liposomes. It is likely that the lower quantity of free liposomes resulting from method 3 is due to the increased interaction of free liposome and DNA, closer to the predicted 1:6 ratio.

The profile resulting from method 3 complexes also shows populations residing a much lower densities than those produced by methods 1 and 2, further supporting the notion of greater DNA/liposome association in method 3 complexes. In addition, method 2 complexes, which are shown in Table 1 to have the largest mean diameter, also produce profiles with high density populations and a significant amount of free liposome. This method was designed to induce the interaction between product (complexes) and starting material (DNA and liposomes) by slower addition of DNA. Complexes produced in this manner tend toward the 1:3 charge neutrality ratio and, therefore, are closer to the point of precipitation.

The profile for complexes produced by method 3 also shows several different populations of DNA/liposome complexes. The number of different populations produced by this method may reflect a relatively high rate of attraction between the cationic lipid and negatively charged DNA. Though the method of complexation was designed to reduce the interaction between product and starting material, apparently the rates of attraction between DNA, liposome and complex are sufficiently high to produce several distinct populations.

Figure 4:
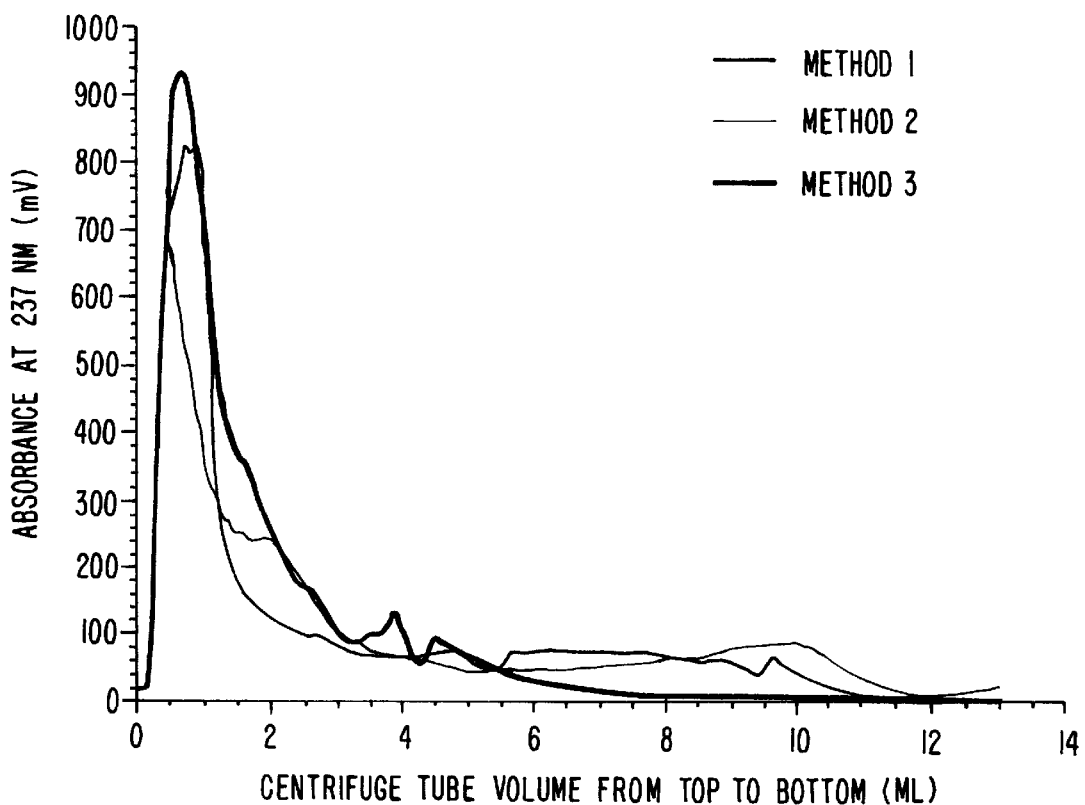
FIG. 4 shows the density gradient profiles of DNA:cationic lipid complexes (1:12 ratio). Profiles are measured by flow-cell UV spectrophotometer at 237 nm. The contents of the centrifuged samples (approx. 13 ml) are pumped through the flow-cell at a rate of 1 ml/min. The ordinate represents the approximate location within the centrifuge tube.

FIG. 4 shows the density gradient profiles for complexes produced at a 1:12 DNA:cationic lipid ratio. For each of the three methodologies, there does not appear to be significant differences in the DNA-containing populations as compared to the 1:6 complexes. The quantity of free liposome, however, is significantly higher for the 1:12 complexes.

Figure 5:
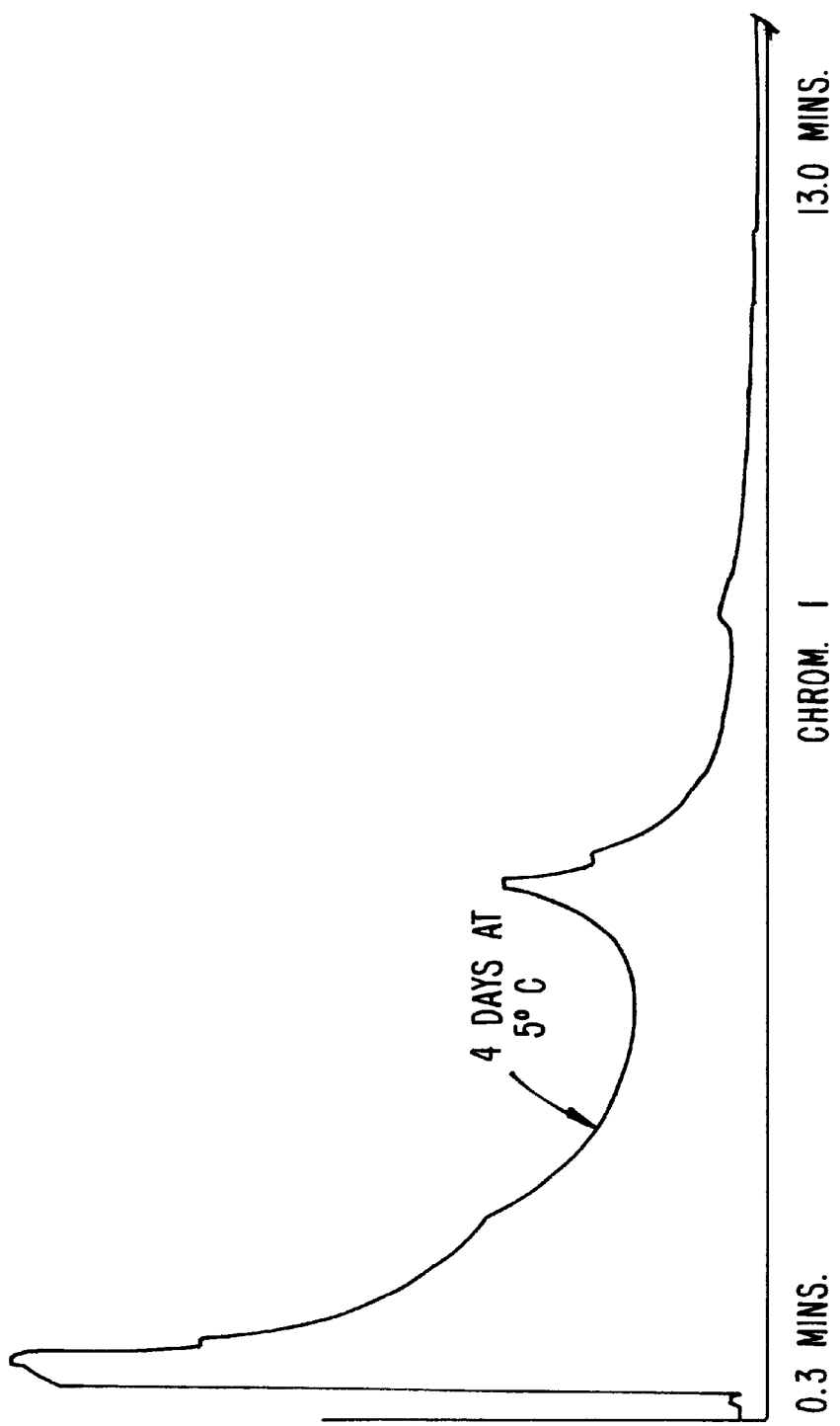
FIG. 5 shows the density gradient profile of DNA-cationic lipid complexes prepared according to the dual feed stream method. Profiles are measured by flow-cell UV spectrophotometer at 237 nm. The contents of the centrifuged samples (approx. 13 ml) are pumped through the flow-cell at a rate of 1 ml/min. The ordinate represents the approximate location within the centrifuge tube.

In a separate experiment, DNA-lipid complexes were prepared at a 1:6 ratio according to Method 3. The resulting complexes were analyzed by glucose density gradient centrifugation after 4 days at 5° C. The resulting profile is shown in FIG. 5. The density gradient profile of these complexes shows a more homogeneous population of DNA-lipid complexes than obtained using Methods 1 and 2.

The data in Table 1 show slight variations in OD400, size and zeta potential between the 1:6 and 1:12 complexes. Since each of these measurements are based on mean values of entire populations, however, the differences may simply be due to the presence of excess free liposome. Centrifugation profiles show similar results with the exception of the additional free liposome. Populations associated with DNA/liposome complexes appear to be the same in both formulations.

Figure 6:
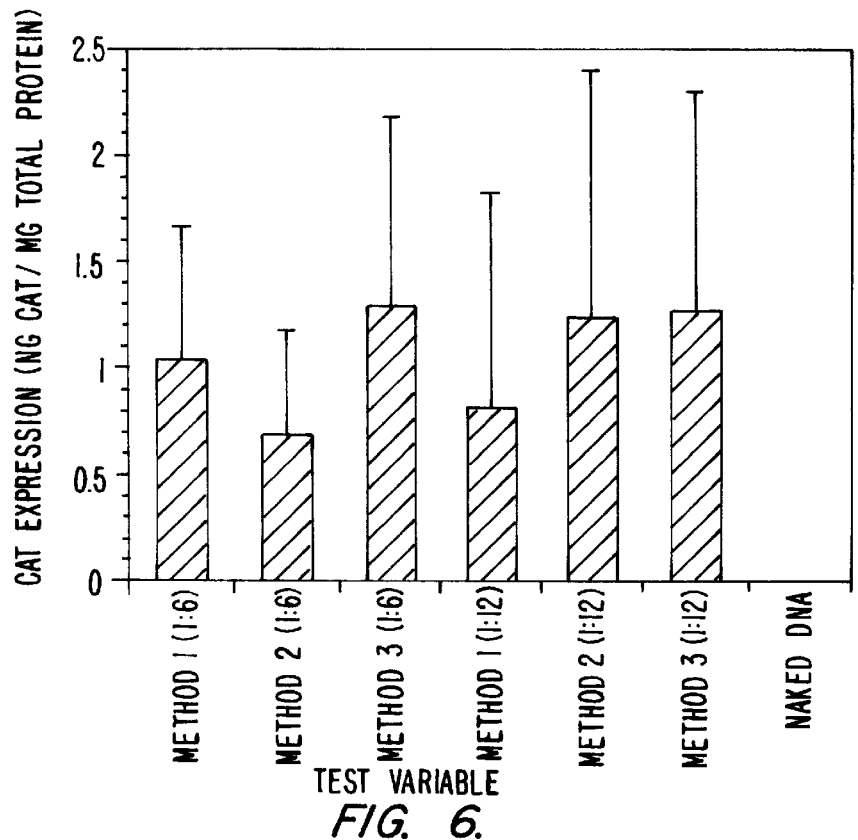
FIG. 6 is a histogram showing the levels of transfection obtained in lung tissue, as measured by CAT expression, resulting from transfection of a CAT reporter plasmid using complexes prepared by the methods described in the Examples that follow.

In vivo expression. FIG. 6 shows the expression level of CAT detected in the lung of ICR mice (n=6), 24 hr post-injection. Though the variability of CAT expression is high in each of the test variables, we do observe significant levels of CAT expression compared with naked DNA. All methods and DNA: cationic lipid ratios appear to produce similar levels of expression.

Example 4

Comparison of Feed Stream Parameters on Preparation of DNA/Liposome Complexes

The following experiments were performed to determine feed stream parameters for preparation of DNA/liposome complexes as described above. Successful preparation was determined by particle size analysis using a NiComp 370 sub-micron particle sizer (Particle Sizing Systems Inc., Santa Barbara, Calif.) and visual inspection for precipitation. The data in Table 2 shows the system configurations and the parameters tested, where Re is the calculated Reynolds' number for flow through a smooth tube.

TABLE 2

| System | Inlet tubing size (I.D.) | Outlet tubing size (I.D.) | Inlet flow rates (ml/min) | Inlet velocity (cm/sec) | Inlet Re | Outlet flow rate (ml/min) | Outlet velocity (cm/sec) | Outlet Re |
|---|---|---|---|---|---|---|---|---|
| 1 | 0.8 mm | 2.4 mm | 10–70 | 33–233 | 264–1864 | 20–140 | 7.4–52 | 178–1248 |
| 2 | 0.3 mm | 2.4 mm | 5–15 | 118–353 | 354–1059 | 10–30 | 3.7–11 | 89–265 |
| 3 | 0.3 mm | 0.8 mm | 2.3–13.5 | 54–318 | 162–954 | 4.6–27 | 15.3–89.5 | 122–716 |

The results shown in Table 2 indicate that a correlation exists between the outlet Re and the ability to produce complexes without precipitation. From these data we can define a lower limit parameter of an outlet Reynolds' number no less than 180–250. It must be emphasized that the calculated Reynolds' number is defined for a smooth tube. Any alterations to the interior of the tube to increase "roughness" can create sufficient mixing conditions at lower Reynolds' numbers (calculated as above).

TABLE 3

| System | Inlet Flow rate | Outlet velocity | Outlet Re | Particle size | Visual Inspection |
|---|---|---|---|---|---|
| 1 | 10 | 7.4 | 178 | N/A | precipitated |
|   | 15 | 11.1 | 266 | 421 ± 286 | cloudy |
|   | 20 | 14.8 | 355 | 282 ± 126 | opalescent |
|   | 30 | 22.2 | 533 | 211 ± 61 | opalescent |
|   | 40 | 30 | 720 | 210 ± 54 | opalescent |
|   | 50 | 37 | 888 | 209 ± 53 | opalescent |
|   | 70 | 52 | 1248 | 212 ± 56 | opalescent |
| 2 | 15 | 11 | 267 | 239 ± 99 | opalescent |
|   | 10 | 7.3 | 178 | N/A | precipitated |
|   | 5 | 3.7 | 89 | N/A | precipitated |
| 3 | 13.5 | 89.5 | 716 | 217 ± 68 | opalescent |
|   | 7 | 45 | 358 | 221 ± 77 | opalescent |
|   | 2.3 | 15.3 | 122 | N/A | precipitated |

The upper limit flow rate was determined by the limitations of the syringe pump used in the experiments. Using an outlet tubing size of 0.3 mm I.D. and an inlet flow rate of 50 ml/min, an outlet flow velocity of 2358 cm/sec was generated and was capable of producing DNA/liposome complexes without precipitation. The calculated inlet Reynold's number for this system was 7074. The integrity of the DNA for this system was determined by quantitation of supercoiled and open circled forms before and after processing. The data show that no significant degradation of DNA occurs during these processes. Although an upper failure limit cannot be defined at this time, the data suggest that complexes can be produced at high Reynolds' numbers (at least 7100) without DNA damage.

Example 5

Preparation of DNA and Liposomes using a Static Mixer

This study compares the formation of DNA/catatonic liposome complexes using a small-scale diluter (10 ml) and static mixer (>7 ml capacity).

Plasmid DNA was provided at a concentration of approximately 5 mg/ml in 10 mM Tris-HCL, pH 8.0.The DNA was diluted to a concentration of 0.5 mg/ml using 5% w/v dextrose. Liposomes were prepared at a concentration of 20 mM. ethyl-dimyristoyl-phosphatidylcholine (EDMPC)/ 20 mM Diphytanoyl-phosphatidylethanolamine (DipPE). The liposomes were diluted to a concentration of 4 mM EDMPC/ 4 mM DipPE. Using the procedures described below, DNA/cationic liposome complexes were prepared by mixing equal volumes of the diluted DNA and liposome solutions.

A. Diluter Method

The diluter method of DNA/liposome complex production is by equal volume addition of DNA to a continuously mixed dispersion of liposomes. The addition rate, type of mixer, and mixing speeds were optimized to produce the desired particle size for the specific geometry of the vessel used. With this procedure, the parameters must be re-optimized as the vessel geometry is changed with scale. Mixing configurations are important in production and must be tightly controlled.

Five ml of the diluted liposome dispersion was added to a sterile 24 ml glass vial. A stirbar, of defined geometry, was added and rotated at speed of approximately 800 rpm. An equal volume of DNA (5 ml) was added at a rate of 1.25 ml/min using a Hamilton microlab diluter, Model #500 series (Reno, Nev.).

B. Static Mixer Method

Equal volumes of 0.5 mg/ml DNA and 4 mM EDMPC/ 4 mM DipPE liposomes were combined into a single feed stream and run through a 21 element, Kenics static mixer yes (Chemineer, North Andover, Mass.) at inlet flow rates of 80 ml/min, corresponding to a linear flow rate of 0.45 feet per second. The final complexes were collected in a 50 ml sterile centrifuge tube.

Following preparation of the complexes, several physical and chemical parameters were tested to analyze the differences in the two methods. Among these tests were particle size, turbidity, zeta potential, pH, and DNA and lipid integrity tests (HPLC, thin layer chromatography, and agarose gel electrophoresis). There were no significant differences in the physical characteristics of the complexes. No significant difference in chemical composition or degradation was observed. The particle size range of the complexes made by the static mixer was tighter than those made by the diluter method as shown in Table 4. Importantly, complexes prepared by either method showed equivalent transfection efficiencies when tested in vivo by intraperitoneal injection of 250 $\mu$l of complex into SKOV-3 tumor-bearing Balb/C nude mice. Tumors were remove 24 hours post injection and assayed for the presence of chloramphenicol acetyltransferase (CAT) reporter protein.

TABLE 4

| Assay | Diluter Method | Static Mixer Method |
|---|---|---|
| Particle size (nm) | 134 | |
| Average | | 162 |
| Minimum | | 161 |
| Maximum | | 162 |
| Std. Dev. | | 0.6 |
| Count | | 3 |
| In vivo expression (pg/mg total protein) | 40 ± 30 | 100 ± 150 |

Example 6

This experiment shows the effect of increasing flow rate on turbidity (optical density at 400 nm), complex size (nm), cationic carrier integrity and DNA integrity. Complexes were prepared using the components and the static mixer method described above, at the flow rates shown in Table 5. These data show that production of a polynucleotide transfection complex using the static mixer can be accomplished across a wide range of flow rates with minimal effect on the physical and chemical characteristic of the starting material. The Reynold's number of the feed streams associated with the tested flow rates indicate flow within the laminar flow regime in most cases (Note Re above 1000 with static mixer is consider to be turbulent flow). The risk of damage to the starting material is, therefore, lower than that resulting from the dual-feed stream method described in Example 5. The data are summarized in Table 5.

TABLE 5

| Linear flow velocity (ft/sec) | Reynold's number | Turbidity (400 nm 1:20 dilution) | Complex particle size (nm) | DNA integrity (Agarose gel) |
|---|---|---|---|---|
| 0.17 | 245 | 0.10 | 269 ± 143 | minimal degradation |
| 0.31 | 446 | 0.08 | 189 ± 82 | minimal degradation |
| 0.56 | 803 | 0.08 | 189 ± 86 | minimal degradation |
| 0.81 | 1164 | 0.08 | 188 ± 91 | minimal degradation |

All publications and patent applications cited herein are hereby incorporated by reference to the same extent as if fully set forth herein. The invention now being fully described, it will be apparent to one of ordinary skill in the art that many changes and modifications can be made thereto without departing from the spirit or scope of the appended claims.

We claim:

1. A method of preparing a polynucleotide transfection complex, said method comprising:

providing a first feed stream comprising a polynucleotide in solution and a second feed stream comprising a polycation in solution;

mixing the first and second feed stream using a static mixer whereby polynucleotide transfection complexes are formed in solution; and removing the solution of polynucleotide transfection complexes.

2. The method according to claim 1 wherein the polynucleotide is DNA.

3. The method according to claim 1 wherein the polycation is selected from the group consisting of cationic lipid, polylysine, polyarginine, and polyhistidine.

4. The method according to claim 3 wherein the polycation comprises a cationic lipid.

5. The method according to claim 4 wherein the polycation further comprises a neutral lipid.

6. A method of preparing a polynucleotide transfection complex comprising:

providing a first feed stream comprising polynucleotides in solution and a second feed stream comprising cationic liposomes in solution;

mixing the first and second feed stream using a static mixer whereby polynucleotide transfection complexes are formed in solution; and removing the solution of polynucleotide transfection complexes.

7. The method according to claim 6 wherein the mixing of the first and second feed streams occurs in a static mixer.

8. The method according to claim 6 wherein the polynucleotide is DNA.

* * * * *